United States Patent [19]
Taylor

[11] Patent Number: 5,230,767
[45] Date of Patent: Jul. 27, 1993

[54] FLOWER PRESS

[76] Inventor: Nancy Taylor, P.O. Box 1298, Lexington, S.C. 29071

[21] Appl. No.: 804,770

[22] Filed: Dec. 9, 1991

[51] Int. Cl.$^5$ .............................. B29C 33/42
[52] U.S. Cl. ........................ 156/580; 156/57; 156/242; 156/245; 156/500; 24/31 V; 24/442; 100/36; 100/297; 34/95
[58] Field of Search .............. 156/57, 242, 245, 500, 156/580; 24/31 V, 442; 100/36, 297; 34/95

[56] References Cited

U.S. PATENT DOCUMENTS

| | | | |
|---|---|---|---|
| 1,283,992 | 11/1918 | Walkup | 156/57 |
| 1,949,268 | 2/1934 | Clark | 156/57 |
| 3,461,511 | 8/1969 | Perina | 24/31 V |
| 3,731,348 | 5/1973 | Luehne | 24/442 |
| 3,852,891 | 12/1974 | Stephen | 34/95 |
| 5,120,300 | 6/1992 | Shaw | 24/442 |

FOREIGN PATENT DOCUMENTS

| | | | |
|---|---|---|---|
| 2535251 | 5/1984 | France | 156/57 |
| 16801 | 1/1984 | Japan | 156/57 |
| 109501 | 6/1985 | Japan | 156/57 |
| 169401 | 9/1985 | Japan | 156/57 |

Primary Examiner—Caleb Weston
Attorney, Agent, or Firm—Michael A. Mann

[57] ABSTRACT

A flower press comprising a top plate and a bottom plate with layers of two materials therebetween and straps with VELCRO tabs to secure the press and apply the pressure for pressing flowers therein. The first layer is preferably cardboard to offer firm support for leaves and petals but not crush stems; the second layer is preferably absorbent paper. Two layers of paper are placed between two layers of cardboard. The top plate is preferably made of a transparent material so that it can be used for later display of the pressed floral arrangement.

10 Claims, 1 Drawing Sheet

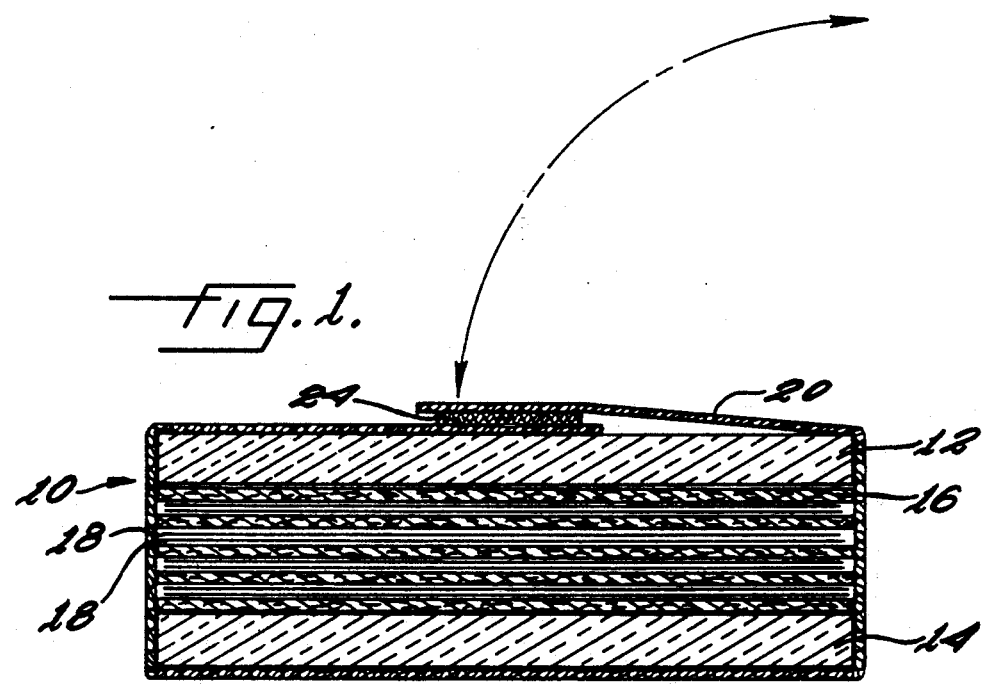
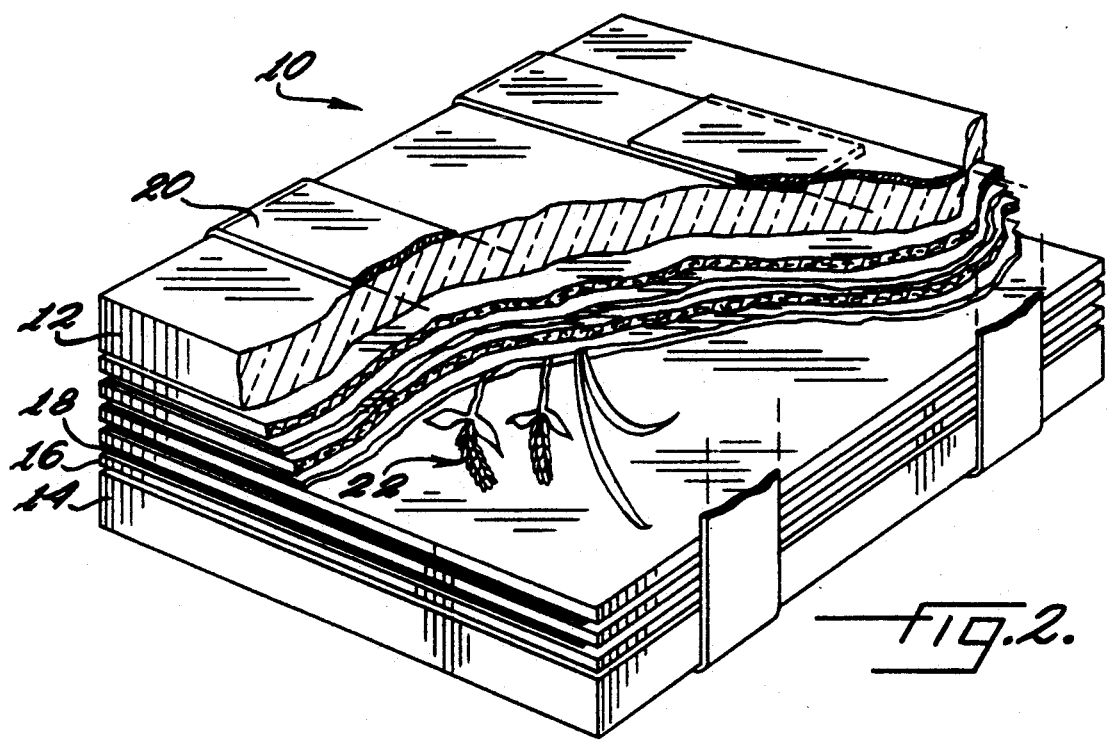

FLOWER PRESS

BACKGROUND OF THE INVENTION

1. Field of the Invention

The present invention relates to flower presses.

2. Discussion of Background

Pressing flowers to preserve them and to make static, two-dimensional arrangements of them for decorations is a well known craft. One typical flower press comprises two frames with bolts through the corners and wing nuts for exerting pressure. Simpler arrangements using heavy books as a source of pressure on the flowers with absorbent paper between the books have also been used.

These types of presses are unsatisfactory. Turning four wing nuts may produce sufficient force but is slow. Using books may not produce enough force and is simply make-shift and cumbersome.

SUMMARY OF THE INVENTION

According to its major aspects and broadly stated, the present invention is a device for pressing flowers. The device comprises two spaced apart plates with layers of cardboard therebetween. Between each cardboard layer are two layers of an absorbent material such as paper. Two straps encircle the plates. The straps have VELCRO tabs on their ends so that the force of the straps holding the plates together can be varied by adjusting the VELCRO tabs to change the tension on the straps. Preferably the top plate is transparent; most preferably, both plates are made of clear Plexiglass.

The transparent top plate is an important feature of the present invention. Being transparent, and preferably clear, the top plate allows information to be presented to the buyer by sliding it behind the clear top plate. Furthermore, the top plate can be used as a cover in framing the pressed flowers.

The VELCRO straps are another important feature of the present invention. VELCRO fasteners are easily, quickly and infinitely adjustable and can hold the two plates together firmly.

Yet another important feature of the present invention are the interior layers. Both absorbent and crushable layers are used, with two layers of absorbent paper used between each two layers of crushable material. The crushable material is preferably cardboard so that any hard portion of the flowers such as the stems can crush the cardboard but soft parts such as petals are held firmly by the cardboard.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a side, cross-sectional view of a flower press according to a preferred embodiment of the present invention; and FIG. 2 is a perspective view of the flower press according to a preferred embodiment of the present invention.

DETAILED DESCRIPTION OF A PREFERRED EMBODIMENT

Referring now to FIGS. 1 and 2, there is illustrated a flower press according to a preferred embodiment of the present invention. The press, generally indicated by the reference character 10, comprises a top plate 12 and a bottom plate 14. Between top plate 12 and bottom plate 14 are a plurality of first layers 16 and a plurality of second layers 18. A pair of straps 20 encircle press 10 to apply pressure to top plate 12 and bottom plate 14.

Flowers 22, or other organic matter including such items as weeds, moss, and grains, are placed between second layers 18 which are preferably made of an absorbent material such as paper, preferably an especially absorbent paper such as the type with a high rag content. First layers 16 are preferably a relatively firm but crushable material such as cardboard. Cardboard offers resistance up to a point and then yields. For stems, crushing is not desirable and cardboard will yield when pressed against the stems but would offer firm support for petals and leaves.

Top plate 12 must, of course, be made of a firm, unbending material and is preferably made of Plexiglass or glass so as to be transparent. Bottom plate 14 is conveniently made of the same material but may be made of any firm, unbending material. Transparency does not contribute to the capability of top plate 12 and bottom plate 14 and of straps 20 to press flowers. However, the advantage of a transparent top plate is two-fold. In the sale of the flower press, information and advertising can be placed behind top plate 12 so that it is visible through top plate 12 and so that press 10 forms its own package and the information can be easily changed. The second advantage of a transparent top plate 12 is that it can be used as a cover in framing the pressed flowers.

Straps 20 are preferably made of a fabric and most preferably a somewhat stretchable fabric with tabs 24s of VELCRO on the ends. The strips of VELCRO are preferably long enough to allow different tension on straps 20 and still hold securely. Two straps are sufficient for smaller presses; more for larger ones. Although VELCRO is preferred, the important features of VELCRO are its ease of attachment and detachment, its infinite adjustability and its non-abrasive structure.

The number of first layers 16 and second layers 18 depends on intended use. It is important to have at least two first layers 16 and at least two second layers 18, the two second layers 18 between two first layers 16 so that absorbent material is on both sides of flowers 22. Additional layers can be used to press several flowers that may eventually be combined in a single display.

In use, straps 20 are spread on a surface, parallel to each other, and bottom plate 14 is placed thereon and centered. One first layer 16 is placed on bottom plate 14, then one second layer 18 placed on first layer 16. Flowers 22 are placed on second layer 18, then another second layer placed on flowers 22. Another first layer 16 is placed on this second layer. Layers can be added as desired until all flowers 22 are covered by a second layer 18 and a first layer 16. Top plate 12 is placed on top of the stack of first and second layers 16, 18. Then straps 22 are joined to encircle press 10 and adjusted to the desired tension.

It will be apparent to those skilled in the art that many changes and substitutions can be made to the preferred embodiment herein described without departing from the spirit and scope of the present invention as defined by the appended claims.

What is claimed is:

1. A device for pressing flowers, said device comprising:
   a first plate;
   a second plate, said second plate spaced apart from and opposing said first plate;
   a plurality of first layers positioned between said first and said second plates for pressing said flowers between said first and second plates, said plurality of said first layers made of cardboard;
   a plurality of second layers positioned between said first and said second plates, two of said plurality of second layers located between each two of said plurality of said first layers; and
   at least one strap for encircling said first and said second plates, each strap of said at least one strap having a first end and a second end, said strap having means for joining said first end to said second end so that said strap can apply an effective amount of force on said first and said second plates to press any flowers between said plurality of second layers.

2. The device as recited in claim 1, wherein said joining means further comprises VELCRO tabs.

3. The device as recited in claim 1, wherein said first plate is made of a rigid, transparent material.

4. The device as recited in claim 1, wherein said at least one strap is two straps.

5. The device as recited in claim 1, wherein said plurality of said second layers are made of absorbent paper.

6. A device for pressing flowers, said device comprising:
   a first plate, said first plate being transparent;
   a second plate, said second plate spaced apart from and opposing said first plate;
   a plurality of first layers positioned between said first and said second plates, said plurality of first layers made of cardboard;
   a plurality of second layers positioned between said first and said second plates, said plurality of second layers made of a material adapted for engaging said flowers; and
   means for pressing said first and said second plates together to press any flowers between said plurality of second layers.

7. The device as recited in claim 6, wherein said two layers of said plurality of second layers are positioned between each two layers of said plurality of said first layers.

8. The device as recited in claim 6, wherein said second layers are made of an absorbent material.

9. The device as recited in claim 6, wherein said forcing means further comprises a pair of straps, each strap having tabs of VELCRO for joining the ends of said straps.

10. A device for pressing flowers, said device comprising:
    a transparent first plate;
    a second plate, said second plate spaced apart from and opposing said first plate;
    a plurality of first layers positioned between said first and said second plates, said plurality of first layers made of cardboard;
    a plurality of second layers positioned between said first and said second plates, two of said plurality of second layers located between each two of said plurality of said first layers, said plurality of second layers made of an absorbent material; and
    two straps for encircling said first and said second plates, each strap having tabs carrying VELCRO for joining the ends of said straps together so that said first and said second plates are pressed together whereby any flowers between said plurality of said second layers are pressed.

* * * * *